United States Patent [19]

Laszczower

[11] 4,321,921
[45] Mar. 30, 1982

[54] APPARATUS FOR SUCKING BLOOD OUT OF BODY CAVITIES

[75] Inventor: Max Laszczower, Basel, Switzerland

[73] Assignee: Solco Basel AG, Switzerland

[21] Appl. No.: 66,714

[22] Filed: Aug. 15, 1979

[30] Foreign Application Priority Data

Aug. 17, 1978 [CH] Switzerland .......................... 8717/78

[51] Int. Cl.³ .............................................. A61M 1/00
[52] U.S. Cl. .................................................... 128/276
[58] Field of Search ............... 128/275, 276, 277, 278, 128/281, 297, 302, 91; 433/91, 92

[56] References Cited

U.S. PATENT DOCUMENTS

| 2,637,106 | 5/1953 | Otis | 433/91 |
| 3,520,300 | 7/1970 | Flower, Jr. | 433/91 |
| 3,758,950 | 9/1973 | Krouzian | 433/91 |
| 3,860,001 | 1/1975 | Levin | 128/276 |
| 3,891,416 | 6/1975 | Leonard et al. | 128/276 |
| 4,158,916 | 6/1979 | Adler | 433/91 |

Primary Examiner—Robert W. Michell
Assistant Examiner—J. L. Kruter
Attorney, Agent, or Firm—Neil F. Markva

[57] ABSTRACT

An apparatus for sucking blood out of body cavities blood collecting vessel is at one end connected via a flexible line to a source of vacuum, and, at the other provided integrally with a suction tube. The lower portion of the suction tube includes suction orifices and projects into a basket acting as a filter carrier. This basket includes a series of suction slots located only in the lower part of the wall of the basket to avoid aspiration of air. On its outer surface, the basket is surrounded by a filter fabric which is fixed in an annular groove. Structures alternative to the basket are also disclosed.

8 Claims, 5 Drawing Figures

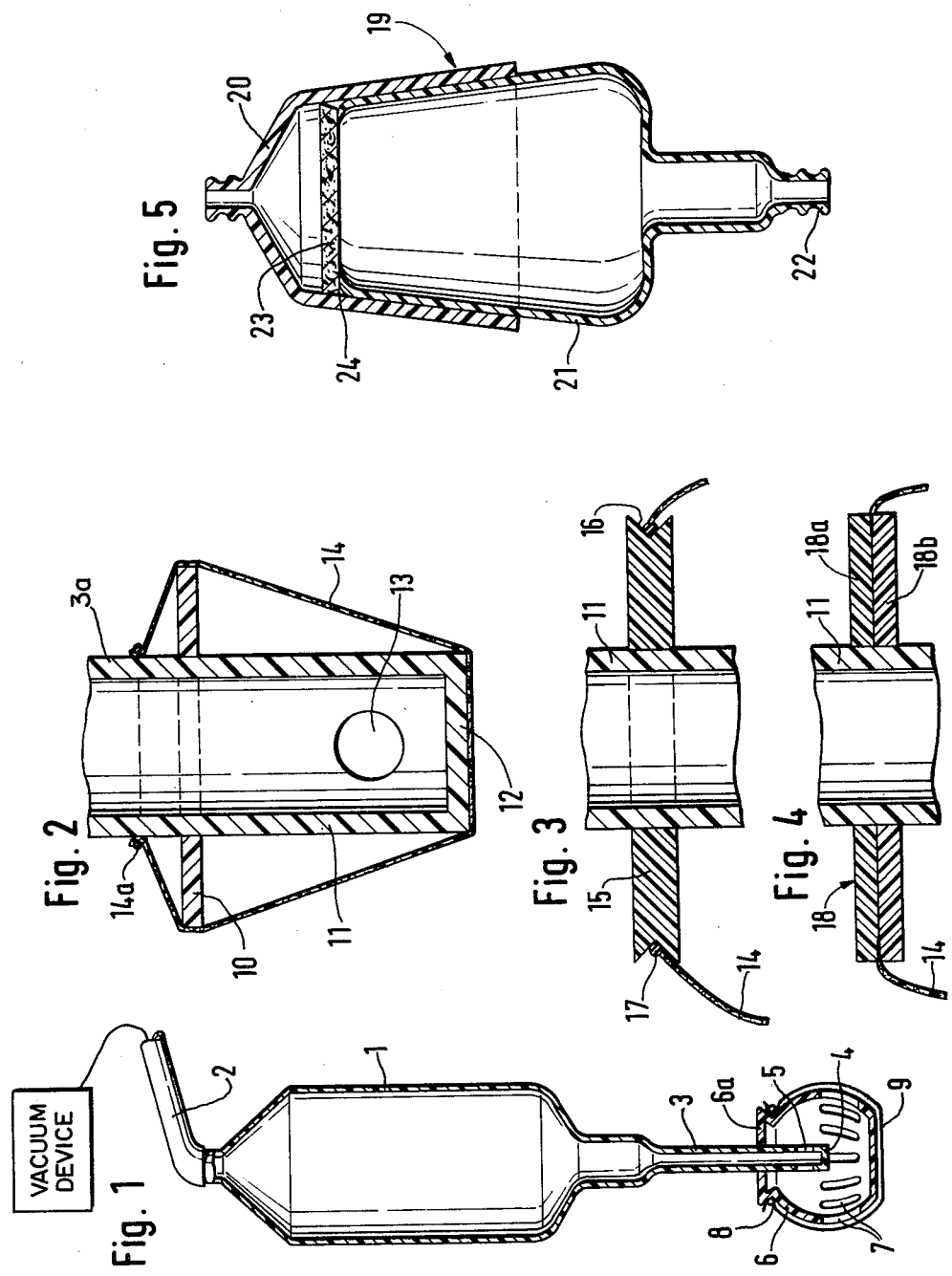

APPARATUS FOR SUCKING BLOOD OUT OF BODY CAVITIES

FIELD OF THE INVENTION

The present invention relates to apparatus for sucking blood out of body cavities.

BACKGROUND OF THE INVENTION

In certain emergency situations, such as tubal rupture or rupture of the spleen or kidney, and in the course of surgery on the heart and on the major blood vessels, severe bleeding may occur in the abdominal cavity or in the thoracic cavity. The amount of blood flowing out during such bleeding can be several liters. Various known devices collect this blood and reintroduce (re-infuse) it into the circulatory sustem of the patient. Though blood banks are nowadays in most cases in a position to make available the number of suitable conserved blood units required for such an emergency, there are important arguments in favor of re-infusion, namely, reliable compatibility in respect of blood group and blood factors, no danger of transmission of hepatitis, immediate availability of a substantial amount of blood and, not least of all, the fact that the cost of conserved blood has risen. The oldest method is to scoop the blood out of the abdominal cavity with a large spoon, filter it through several layers of gauze and infuse it into the patient through a funnel. More recently, an apparatus has been described which sucks the blood through a suction tube into a collecting vessel from which it can be re-infused into the patient. The suction tube used for this purpose is open at the free end and cannot prevent blood clots because intestinal wall or omentum may be occasionally sucked against it, thereby interrupting the stream of blood into the collecting vessel. The rather long pipeline from the suction tube to the collecting vessel, and a part of the vessel, must be filled with a physiological salt solution before beginning to suck out the blood. The entire process is involved and requires a specially trained person to use this apparatus.

SUMMARY OF THE INVENTION

The present invention seeks to simplify the sucking out of blood from the abdominal cavity or thoracic cavity and to filter the blood before it ever enters the collecting vessel, by a particular design of the suction tube. At the same time, the aspiration of blood clots or of parts of the intestinal wall or of omentum is to be avoided. Otherwise the flow of blood from the body cavity into the collecting vessel would be interrupted. The entire process should take place in such a way that it does not differ essentially from a common blood transfusion and that special training in handling the apparatus is unnecessary.

Further the occurrence of turbulence in the blood in the region of the suction orifice or orifices is to be prevented, since it is known that such turbulence mechanically damages a part of the red blood corpuscles, and this can lead to haemolysis.

According to the present invention, the apparatus for sucking blood out of body cavities comprises a collecting vessel including a suction tube having at least one orifice defined therein. A filter means including a filter medium is fixed to the lower end of the suction tube and spaced from said orifices to protect the suction tube orifice or orifices from contact with the filter medium which surrounds the lower end of the suction tube.

BRIEF DESCRIPTION OF DRAWINGS

Other objects of this invention will appear in the following description and appended claims, reference being made to the accompanying drawings forming a part of the specification wherein like reference characters designate corresponding parts in the several views.

FIG. 1 is a simplified cross-sectional view of a first embodiment of apparatus for sucking blood out of a body cavity according to the present invention;

FIG. 2 is an enlarged cross-sectional view of a variant of the lower portion of the suction tube of FIG. 1;

FIGS. 3 and 4 are cross-sectional views of two further variants of the lower portion of FIG. 2, and FIG. 5 is a cross-sectional view of a variant of the collecting vessel of the apparatus of FIG. 1.

DETAILED DESCRIPTION

A collecting vessel 1 is connected via a flexible pipeline 2 to a source of vacuum. The lower part of collecting vessel 1 terminates in a suction tube 3 integrally formed with collecting vessel 1 from a moldable material such as a plastics material. Appropriately constructed stiffening ribs will improve the strength of collecting vessel 1 which is exposed to the difference in pressure between vacuum and atmosphere. Alternatively, suction tube 3 may be produced separately from collecting vessel 1 and connected to it by known means.

The lower end face 4 of suction tube 3 is closed in FIG. 1, but could instead be open. One or more suction orifices 5 are located above end face 4 in suction tube 3. A filter carrier 6 has a virtually oval cross-section and an upper portion 6a fixed to the periphery of suction tube 3.

In this embodiment, filter carrier 6 is composed of plastic material and has several suction slots 7 in its peripheral zone. To avoid undesirable aspiration of air, and hence to avoid frothing within the blood, suction slots 7 only extend over the lower zone, for example, the lower one-third, of the total height of filter carrier 6. Carrier 6 may be injection-molded in one piece from a plastics and has an annular throat or annular groove 8 at the transition to the upper fixing portion or plate 6a. Throat or groove 8 serves to hold a bag-shaped filter fabric 9. Filter fabric 9 can be sealingly suspended in the throat 8 by known means such as an elastic band, and surrounds the entire basket-shaped filter carrier 6 with exception of the upper portion 6a. During the process of sucking out the blood, filter fabric 9 rests against the periphery of filter carrier 6. However, for clarity, filter fabric 9 has been shown at a certain spaced distance from the inside wall of filter carrier 6.

If blood is now to be sucked out by means of the apparatus described, tube 2 is connected to the source of vacuum and first, as usual, an anti-coagulant is sucked into the collecting vessel 1. The collecting vessel 1 can also be wetted with an anti-foam agent. Suction tube 3 is then lowered into the blood so that the suction slots 7 are below the blood level. Hereupon, by virtue of the reduced pressure prevailing within the suction tube 3, the blood first flows through the filter fabric 9, with blood clots or tissue particles being retained on the outer surface of the fabric. The blood then passes through the suction slots 7 into the interior of the filter carrier 6 and from there, through the orifices 5, into the suction tube 3, from where it is sucked upwards into the collecting vessel 1.

In this process of sucking out the blood, the effective filtration of the blood by filter fabric 9 is, above all, of particular importance. Further, suction orifices 5 of the suction tube 3 are absolutely out of range of the region of the filter fabric 9 and hence orifices 5 cannot be blocked by the blood clots and the like adhering to outer surface of the filter fabric 9. During aspiration of the blood, the filter fabric 9 admittedly rests against the outer suction slots 7, but these are of sufficient size that, as experience has shown, slight blockage thereof has no effect on the ability of the apparatus to function.

The blood collected in the manner described is then re-infused into the patient in a known manner, for example using a commercial transfusion line.

FIG. 2 shows a variant of the suction tube of FIG. 1. Here again the lower face 12 of the suction tube 3a is closed and tube 3a includes at least one suction orifice 13. In contrast to FIG. 1, however, the lower portion 11 of suction tube 3a now carries a disc-shaped plate 10 which serves to hold a filter fabric 14. The filter fabric 14 is drawn over plate 10 and the lower end face 12 of suction tube 3a in such a way that it is in the shape of two truncated cones which adjoin at their bases. At the periphery of the portion 11 of suction tube 3a, the upper edge of the filter fabric 14 is held against the periphery of suction tube 3a by fixing means which are in themselves known, for example, an elastic band 14a.

In this embodiment of FIG. 2, the fact that the filter fabric 14 is held on the plate 10 again ensures that the orifices 13 remain at a distance from the filter fabric, thereby reliably avoiding a blockage.

However, in the embodiment of FIG. 2, in contrast to the construction shown in FIG. 1, it is absolutely necessary that the suction orifices 13 of the portion 11 of suction tube 3a should not be present on its lower end face 12 but on the periphery of the suction tube.

The purpose of the plate 10, which is preferably in the shape of a circular disc, is to keep the filter fabric 14 at a distance from the suction orifices 13. In FIG. 3, the filter fabric 14 can also be secured, for example, by the plate 15 having an annular recess or groove 16 on its periphery. The upper portion of the filter fabric 14 is held in recess 16 by an elastic band 17.

The embodiment of FIG. 4 has plate 18 consisting of two virtually identical discs 18a and 18b resting on top of one another. In this embodiment, the upper end portion of the filter fabric 14 is clamped in the edge zone between the two discs 18a and 18b. The discs 18a and 18b can, by known means not shown, on the one hand, be pressed against one another and, on the other hand, be fixed to the periphery of suction tube 11 which corresponds to tubes 3 and 3a of the earlier embodiments.

The filter fabric 9 or 14 is preferably a sock-shaped plastics having a mesh width selected as sufficient to retain reliably even fairly small blood clots or tissue particles.

In the embodiment of FIG. 1, the lower portion of the suction tube 3 preferably has several suction orifices 5 distributed over the periphery of the suction tube. This results in a relatively large aspiration cross-section and, as experience has shown, turbulence in the flowing blood can thereby be avoided. This prevents damage to the red blood corpuscles and reduces the risk of haemolysis.

The apparatus described is of uncomplicated construction and can be operated even by non-specialist personnel after brief practice.

In the variant shown in FIG. 5, the collecting vessel 19 is has an upper part 20 which overlaps a lower part 21 in a vacuum-tight manner. Both parts 20 and 21 have conical walls and match one another so that when pushed into one another they adhere together securely. The lower inner part 21 includes a connection 22 for a suction head which is not shown and carries a filter 23 at its upper end portion which projects into the upper part 20. The filter 23 may be a fabric filter. The filter 23 is anchored in an annular groove 24 and extends over the entire free cross-section of the collecting vessel 19 and primarily serves to filter out or disperse any froth present in the blood.

While the Apparatus for Sucking Blood out of Body Cavities has been shown and described in detail, it is obvious that this invention is not to be considered as being limited to the exact form disclosed, and that changes in detail and construction may be made therein within the scope of the invention, without departing from the spirit thereof.

We claim:

1. An apparatus for sucking blood out of body cavities, said apparatus comprising:
    (a) a collecting vessel including a suction tube having a lower end section with at least one orifice defined therein,
    (b) a filter means including a filter medium and means for fixing an upper edge of the filter medium to the lower end section of the suction tube,
    (c) said filter medium being spaced from said orifice to protect the suction tube orifice from contact with the filter medium which surrounds the lower end section of the suction tube,
    (d) said fixing means being effective to secure the upper edge of the filter medium around the entire periphery thereof and including disk means, laterally displaced from the lower end of the suction tube,
    (e) said disk means including a plate and an annular groove,
    (f) said filter medium including a sock-shaped filter fabric having a free upper end edge, and
    (g) the filter medium fixing means fixes the upper end edge of the sock-shaped filter fabric in the annular groove adjacent the plate.

2. An apparatus according to claim 1, wherein the filter means includes a basket with at least one suction slot and said plate and annular groove defined therein,
    said filter fabric covers the at least one suction slot from the outside of the basket.

3. An apparatus according to claim 2, wherein the at least one suction slot extends over only the lower portion of the basket to avoid aspiration of air if the depth of blood to be sucked out is low.

4. An apparatus according to claim 3, wherein said suction slot is about one third of the height of the basket.

5. An apparatus according to claim 2, wherein the basket defines a chamber around the lower end of the suction tube.

6. An apparatus according to claim 1, wherein the suction tube and collecting vessel are produced integrally as a single unit from a plastics material.

7. An apparatus according to claim 1, comprising a vacuum device for creating a reduced pressure in the collecting vessel.

8. An apparatus according to claim 1, wherein said plate has an outer circumference and is fixed to the lower part of the suction tube, and the annular groove extends along the outer circumference of the plate.

* * * * *